(12) United States Patent
Kleyman et al.

(10) Patent No.: US 12,121,705 B2
(45) Date of Patent: Oct. 22, 2024

(54) SYRINGE PLUNGER FINGER RING STRUCTURES

(71) Applicants: Gennady I Kleyman, Brooklyn, NY (US); Alexander Merson, Brooklyn, NY (US)

(72) Inventors: Gennady I Kleyman, Brooklyn, NY (US); Alexander Merson, Brooklyn, NY (US)

(73) Assignee: Algen & Klemer, LLC., New York City, NY (US)

( * ) Notice: Subject to any disclaimer, the term of this patent is extended or adjusted under 35 U.S.C. 154(b) by 101 days.

(21) Appl. No.: 17/983,540

(22) Filed: Nov. 9, 2022

(65) Prior Publication Data

US 2023/0071582 A1 Mar. 9, 2023

Related U.S. Application Data

(62) Division of application No. 17/137,490, filed on Dec. 30, 2020, now Pat. No. 11,534,552.

(51) Int. Cl.
*A61M 5/31* (2006.01)

(52) U.S. Cl.
CPC ........ *A61M 5/3137* (2013.01); *A61M 5/3148* (2013.01); *A61M 2005/3139* (2013.01); *A61M 2210/0637* (2013.01)

(58) Field of Classification Search
CPC .............. A61M 5/3137; A61M 5/3148; A61M 2005/3139
See application file for complete search history.

(56) References Cited

U.S. PATENT DOCUMENTS

2007/0208310 A1* 9/2007 Stadick ............... A61M 5/3148
604/187

* cited by examiner

*Primary Examiner* — James D Ponton
*Assistant Examiner* — Hong-Van N Trinh (57) ABSTRACT

A syringe finger ring and finger ring inserts, that in various embodiments, provides or connects to a syringe that comprises a syringe body capable of having a volume of material therein and a plunger disposed to enter the syringe body and dispense material from the syringe body by movement of plunger, and a novel a finger ring and related structures having an open area and connected, by various structures, to the plunger adapted to receive a finger within the finger ring open area, including a spacer of various embodiments inserted within the open area to selectively reduce the open area and provide more controllable engagement of the syringe plunger by the operator finger in distal and proximal strokes.

8 Claims, 8 Drawing Sheets

SYRINGE PLUNGER FINGER RING STRUCTURES

Priority is claimed on Non-Provisional patent application Ser. No. 17/137490 filed 30 Dec. 2020, entitled Syringe Plunger Finger Ring Structures and Provisional Patent Application No. 63/071409 filed 28 Aug. 2020, entitled Adjustable Ring Structure For Dental Syringe.

FIELD OF THE INVENTION

The present invention relates to syringes in particular, to conventional and dental syringes having finger receptacle to better engage an operator finger to facilitate comfortable use of the syringes.

BACKGROUND OF THE INVENTION

Conventional and dental syringe used requires skilled and confident, accurate operation (e.g. a controlled compression of a syringe plunger) and simultaneous precise control of the needle location and depth. Moreover, it is very important to precisely accomplish both the distal (injecting) stroke, e.g. to determine whether the needle is in a blood vessel, and the proximal (aspirating) stroke. These qualities are absolutely necessary in cosmetic procedure applications (injection of Botox, fillers etc.) and in dental procedures. Existing conventional and dental syringes typically have limited plunger ring surfaces. This drawback makes it hard to operate and hard to control the dispensing of syringe content. It is also very important to emphasize that the plunger ring surfaces of existing syringes don't accommodate the variety of finger sizes, and don't have any structure to enhance the operation itself or to control of syringes by the user.

SUMMARY OF THE INVENTION

Disclosed is an ergonomically improved conventional and dental syringe including adjustable ring structure that substantially surround the operator finger with portions of the syringe member that receives an operator finger, which facilitates convenient plunger operation and more controllably to accomplish both the distal (injecting) stroke and the proximal (aspirating) stroke.

In various embodiments, the present invention provides or connects to a syringe that comprises a syringe body capable of having a volume of material therein and a plunger disposed to enter the syringe body and dispense material from the syringe body by movement of plunger, and a novel a finger ring and related structures having an open area and connected to the plunger adapted to receive a finger within the finger ring open area, including a spacer of various embodiments inserted within the open area to selectively reduce the open area and provide more controllable engagement of the syringe plunger by the operator finger.

Those embodiments make the syringe significantly more easy, predictable, and controllable to use with both the distal (injecting) stroke and the proximal (aspirating) stroke. The result is a syringe and syringe attachment(s) which enables a reliable and controlled aspiration maneuver and to perform delicate but routine actions, e.g. to test for the presence of blood indicating that a blood vessel has been penetrated, and other critical operations, easily and controllably with one hand.

BRIEF DESCRIPTION OF THE DRAWINGS AND POSITIONS

These and further novel features of the present invention are better understood by taking the following Drawing figures together with the Detailed Description, wherein.

DETAILED DESCRIPTION

Figure 1:
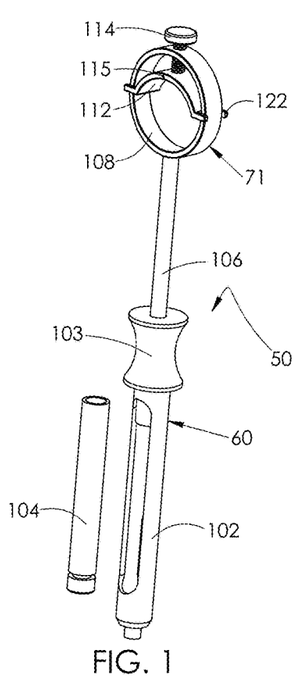
FIG. 1 is an exploded view of dental syringe assembly of a first embodiment.
Figures 2, 3, 4:
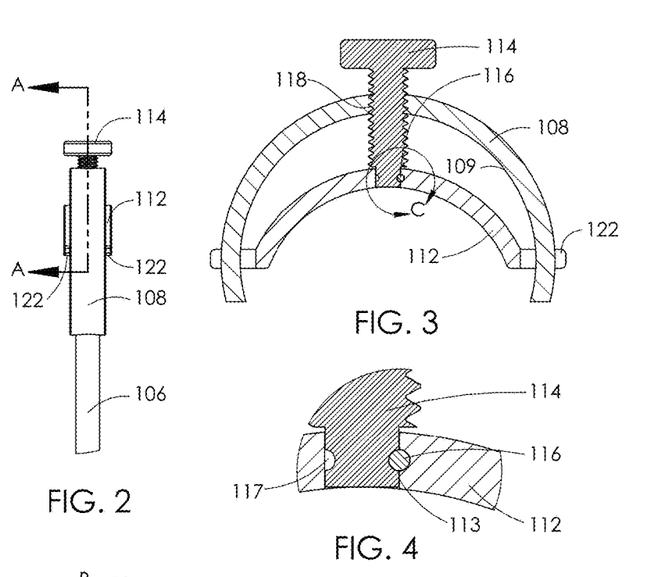
FIG. 2 is a side view of ring assembly in adjusted to finger size position of the embodiment of FIG. 1.
FIG. 3 is a section A-A taken from the embodiment of FIG. 1.
FIG. 4 is an enlarged view C taken from the cross-section A-A of the embodiment of FIG. 1.

A first embodiment 71 according to the present invention is shown in FIGS. 1-4, wherein the syringe 50 of the perspective and side elevation views FIGS. 1 and 2, and cross-sectional and enlarged cross-sectional views of FIGS. 3 and 4, includes a syringe body 102, that typically includes a narrowed or other shaped region 103 for grasping or retention between fingers, and a lower section 60 which receives or includes a cartridge 104 with medication, etc., a piston (not shown) or plunger that compresses a portion of the inserted syringe cartridge 104 by downward movement of a plunger shaft 106 to dispense the medication, and further includes a first ring embodiment 71 on the operating (finger) end of the syringe plunger 106, sized and shaped to accommodate a large finger. The ring embodiment 71 enables the plunger 106 to receive finger compression and withdrawal forces, and includes a movable segment 112, typically a curved elongated member, that is adjustable to more closely fit around inserted fingers ('finger' herein includes thumbs) of varying lesser sizes. For this reason, the dental syringe ring embodiment 71 comprises a ring 108 that includes a threaded hole 118 that retains an adjustment screw 114 that retains and adjusts the relative position of holding segment 112 to fit around a finger (not shown) inserted between the holding segment 112 and the inner surface 109 of ring 108. In the embodiment shown, the holding segment 112 is captive on the end of screw 114 and includes a hole 115 that receives a pin 116 that tangentially engages with screw 114 end circumferential recess 117. When screw 214 end is inserted into the hole 113, the pin 116 in thru hole 115 secures the screw 114 end of the holding segment 112. This engagement permits screw 114 to freely rotate inside hole 115 to move the holding segment 112 relative to the ring 108 according to the screw 114 and ring 108 mating threads. Holding segment guides 122 at the ends of holding segment 112 extend past and partially surround ring 108 and prevents rotation of segment 112 to rotate relative to the ring 108 during screw 114 rotation. Therefore, user rotation of screw 114 moves the segment 112 in syringe axial direction to adjust various openings 'H1, H2. . . ' (e.g. FIG. 12) to accommodate users finger size as tightly as desired. The section A of side elevation view of FIG. 2 is shown in FIG. 3, with an enlarged portion C shown in FIG. 4 showing in greater detail the recess 117 in end of the screw 114 received into the hole 115 and retained by pin 116 that tangentially engages the recess 117, and the holding segment 112, wherein the recess permits rotation of the screw 108 while being retained by pin 116 in segment 112.

Figure 5:
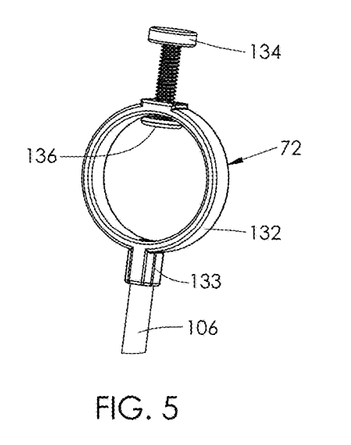
FIG. 5 is an isometric view of ring assembly of a second embodiment.
Figure 6:
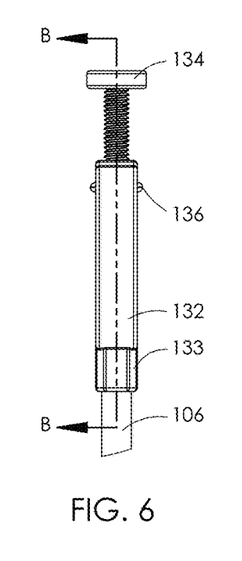
FIG. 6 is a side view of the ring adjustment structure in start position of the embodiment of FIG. 5.
Figure 7:
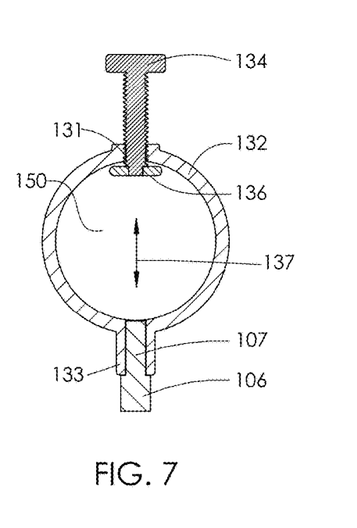
FIG. 7 is a sectional view B-B taken from FIG. 6 of the embodiment of FIG. 5.

A second embodiment 72 of the finger ring is shown in FIGS. 5-7, comprising a ring structure 132 that includes an outward extending tubular member 133 that receives the exposed end 107 of the syringe plunger shaft 106, and further a threaded hole (134 FIG. 7) opposite to the tubular member 133, that receives an adjustable screw similar to screw 114 of the prior embodiment. However, screw 134 disposed in the threaded hole 131, also includes an end that engages and retains a disk member 136 (either fixed or rotatable on screw 134), to be adjustable and rotatable in the threaded hole 131 to move the disk member 136 inwardly to selectively reduce the dimension of the interior region 137 of the finger ring 72.

Figure 8:
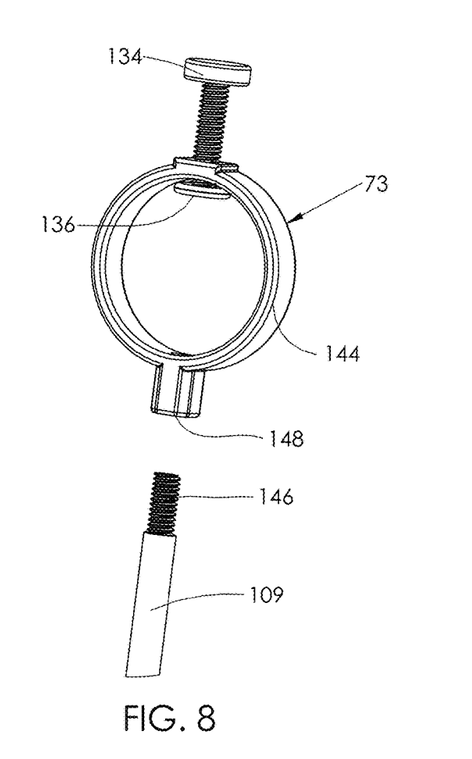
FIG. 8 is an isometric view of ring assembly and syringe plunger shaft of a third embodiment.
Figure 9:
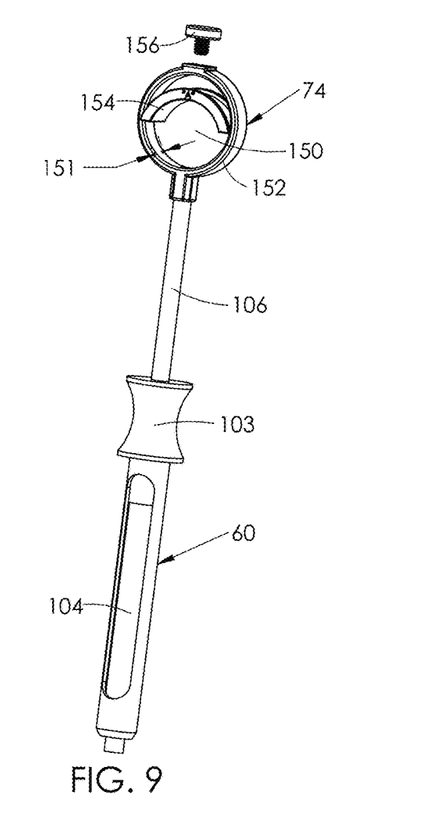
FIG. 9 is an isometric view of ring assembly of a fourth embodiment.
Figure 10:
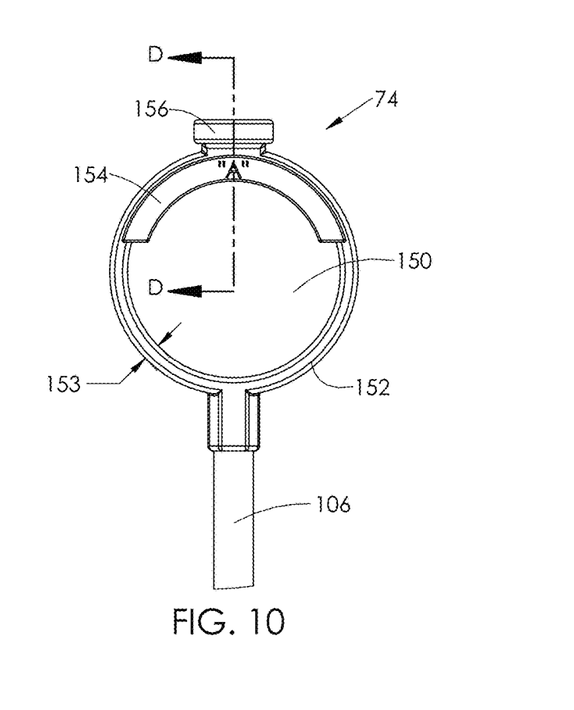
FIG. 10 is a front view elevation of the ring assembly of the fourth embodiment of FIG. 9.

A third embodiment 73 of the finger ring is shown in FIG. 8, wherein the ring structure 144 tubular member 148 is threaded and engages a complementary threaded end 146 of the syringe plunger shaft 106, allowing for the third embodiment 73 to be securely attached to and removable from the syringe plunger shaft. The remaining elements of this embodiment include the elements of the second embodiment discussed above, and other embodiments described herein.

A fourth embodiment 74 is shown in the various view of FIGS. 9-12, wherein the ring 152 is connected to the syringe 60 plunger shaft 106 end 107 (FIG. 7) by a sleeve 133, and has a circumferential wall 153 thickness less than the width 151 so that the ring 152 resembles a short section of a cylinder, and has an inner open area 150. A curved member 154 of various radial thickness having a curvature that permits curved member 154 to nest within the open area 150 and near or against the similarly curved inner surface of a partial radius (<180°) the of the ring 152 to leave the open area 150 largely undiminished except by curved member 154 thickness when adjacent to the inner surface. The curved member 154 may also include raised 'sidewall' portions 155 that provide mechanical strengthening and provide lateral (in the direction of width 151) retention, wherein a curved member 154 upper surface space between sidewall portions 155 is formed that is greater than the width 151 of the ring 152, allowing the curved member to rest against the inner surface of the ring 152 and resist lateral displacement. The length of the curved member 154 and the height of the sidewall portions 155 at the radial ends of the curved member 154 may be extended so as to make the curved member 154 captive within the ring 152, if desired. The curved member 154 radial thickness (into the open area 150) is selected to provide a desired reduction of the open area 150.

Figure 11:
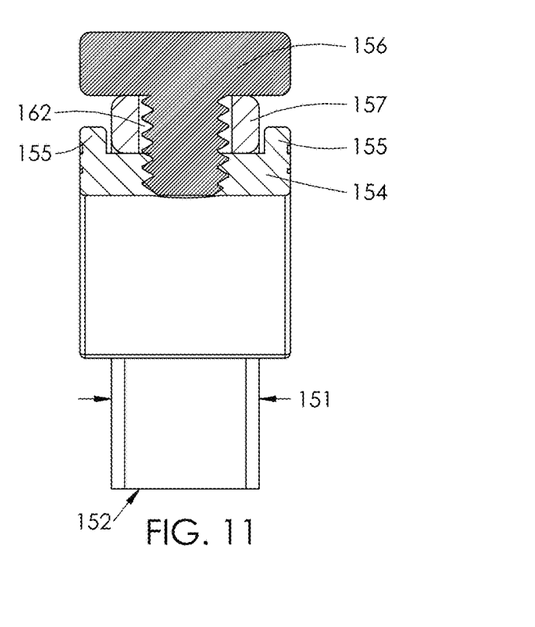
FIG. 11 is a sectional view D-D taken from FIG. 10 of the fourth embodiment of FIG. 9.
Figures 12, 13, 14, 15, 16:
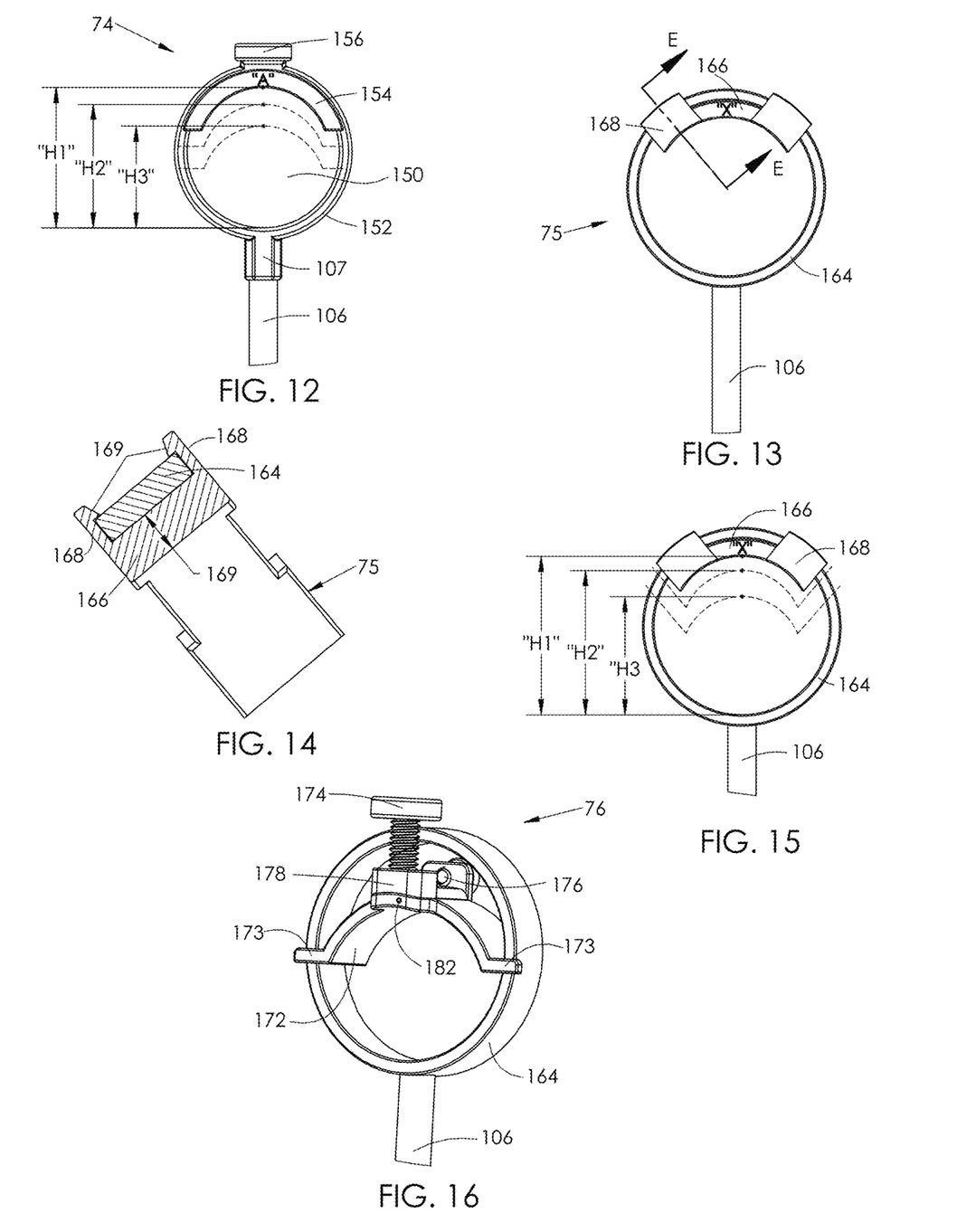
FIG. 12 is a front elevation view of ring of the fourth embodiment of FIG. 9 with inserts "A", "B" and "C"
FIG. 13 front view of the ring assembly of a fifth embodiment.
FIG. 14 is a sectional view E-E taken from FIG. 13 of the fifth embodiment.
FIG. 15 is a front view of ring assembled of the fifth embodiment with inserts "X", "Y" and "Z"
FIG. 16 is an isometric view of ring assembly of a sixth embodiment.

The open area 150 is sized to accept a large finger or thumb, and as shown in FIG. 12, can be reduced to better accommodate a smaller finger or thumb (or provide gripping retention thereof) by inserting a selected curved member 154 into the open area and being secured with screw 156 insertable through a clearance hole 162 through a portion 157 of the cross-section D, FIG. 11, of the ring 154 (typically opposite to the sleeve 133 placement on ring 152) with the curved member retained at the end of the screw 156 as shown in FIG. 4, above. Alternately, the a family of curved members 154 having different thicknesses (into the open area 150) are available and each has a threaded opening to receive the screw 156 for retention within the ring 154 open area 150.

As shown in FIGS. 13-15, a fifth ring embodiment 75 has an annular member 164 has a cylindrical shape similar to annular member 152, above, and is also connected to the plunger shaft 106. A curved member 166, similar to curved member 154 above, and preferably has a radial curvature and length that permits close placement against or near the inner surface of annular member 164. The curved member 166 has radially outward extending 'sidewall' members 168 that are attached at the lateral edges of curved member 166 that has a width sufficient to permit 'sidewall' members 168 to extend past the annular member 164 when seated against the annular member. Furthermore as shown in FIG. 14 cross-section E of FIG. 13, the 'sidewall' members 168 include a tooth 169 to lock the 'sidewall' member on to the annular member 164. A feature of this embodiment is that the open area 150 may be selectively reduced, e.g. H1, H2, H3, by the introduction of curved member's thickness, and a family of different thickness 169 curved members may be available to accommodate different sized fingers or thumbs.

Figures 17, 18:
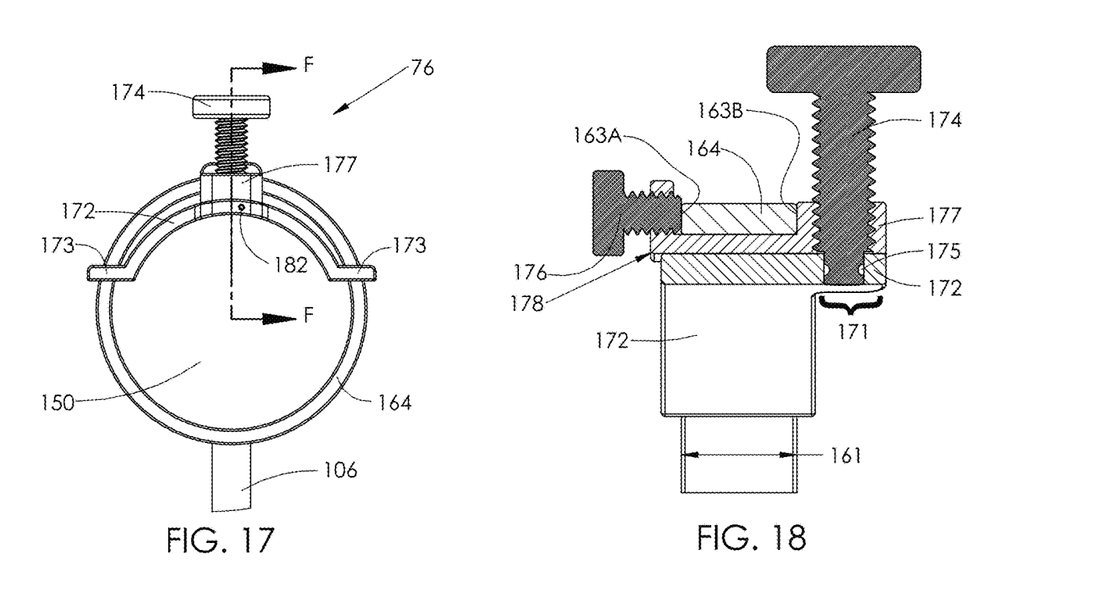
FIG. 17 is a front view of a ring assembly of a sixth embodiment.
FIG. 18 is a sectional view F-F taken from FIG. 17 of the sixth embodiment.
Figure 19:
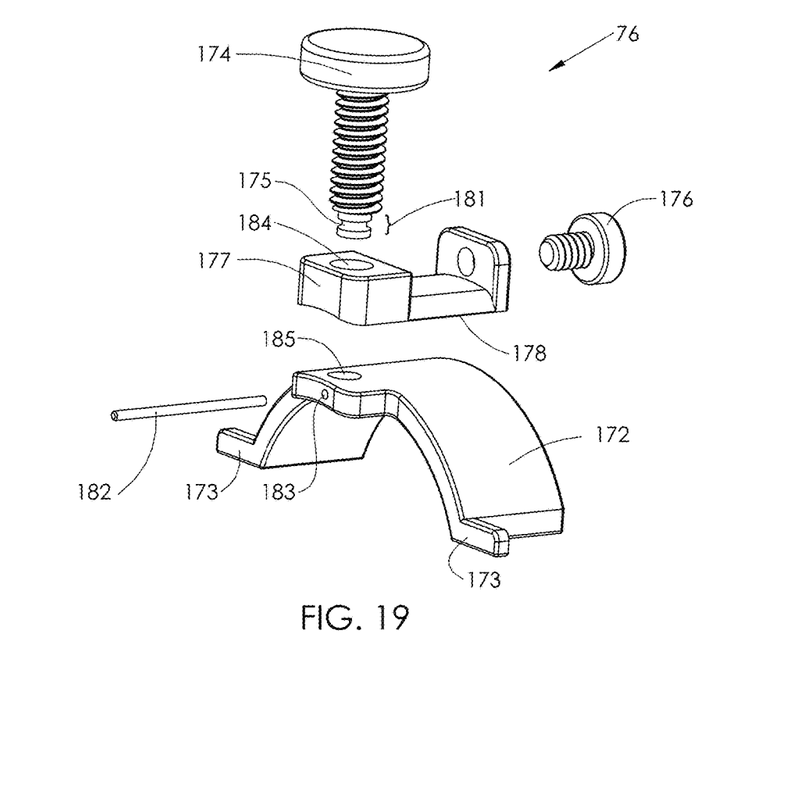
FIG. 19 is an exploded view of an insert assembly of the sixth embodiment.

A sixth embodiment 76 is shown in FIGS. 16-19, that includes a screw 174 adjustment of an insertable inner curved member 172 relative to an threaded holding block 178 retained within the annular member 164 open area 150 by a holding block retaining screw 176, that holding block 164 engages a lateral edge 163A of the annular member 164, and the opposing edge 163B by screw 174 threaded shoulder 177. The lateral movement (in the direction of width 161, FIG. 18) is limited by radially outward extending 'ears' attached to one side of curved member 172 to allow insertion of the assembly of the holding block 178, screw 174, and curved member 172 into the open area 150 of the annular member 164. As shown in FIG. 18 cross-section F of FIG. 17, and exploded view of FIG. 19, the screw end 181 received into lateral extension 171 opening 185, having an circumferential recess 175, is captured by a pin 182 inserted into a curved member 172 lateral extension 171 hole 183 that is disposed sufficiently offset from the center of the lateral extension 171 opening 184 to permit pin 182 to tangentially engage the screw annular recess 175 to retain the screw 174 within the lateral extension 171 hole 183, yet permit rotation that allows the screw 174 to move through threaded shoulder 177 by rotation of the screw 174 causing the curved member 172 to advance into (or retract from) the open area to 'fit' the ring 76 to a particular finger. The curved member 172 is moved inward into the open area 150 and retained there by rotation of the screw 174 and limited in lateral motion by the ears 173, providing a close fitting to and retention by a finger inserted into the open area 150.

Figure 20:
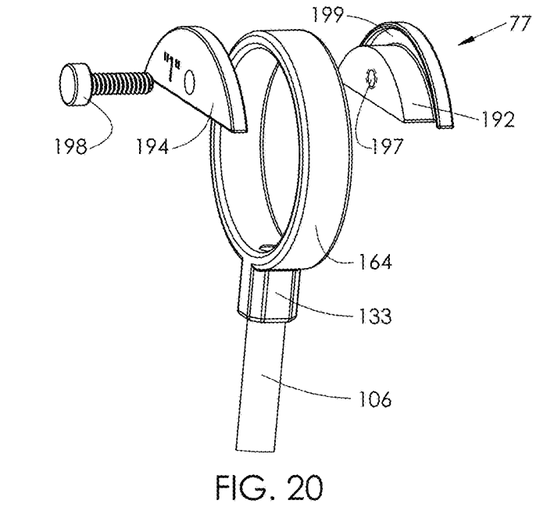
FIG. 20 is an exploded view of inserts assembly with the ring of a seventh embodiment.
Figure 21:
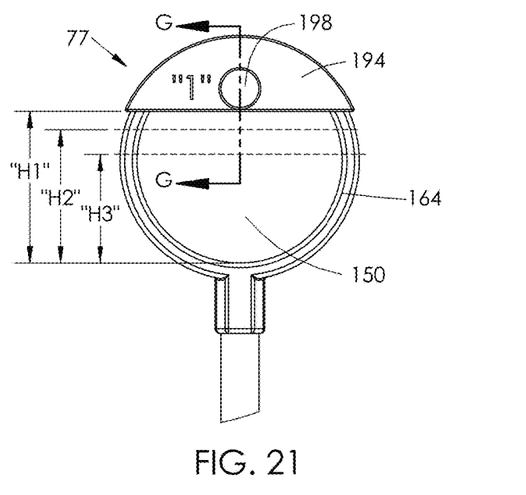
FIG. 21 is a front elevation view of inserts assembled with the ring of the seventh embodiment.
Figure 22:
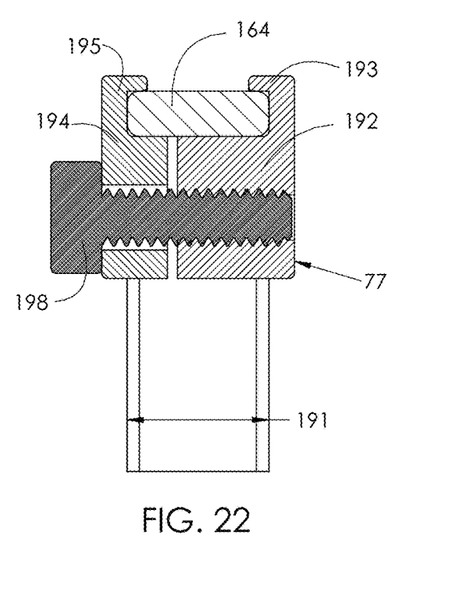
FIG. 22 is a sectional view G-G taken from FIG. 21 of the seventh embodiment.
Figure 23:
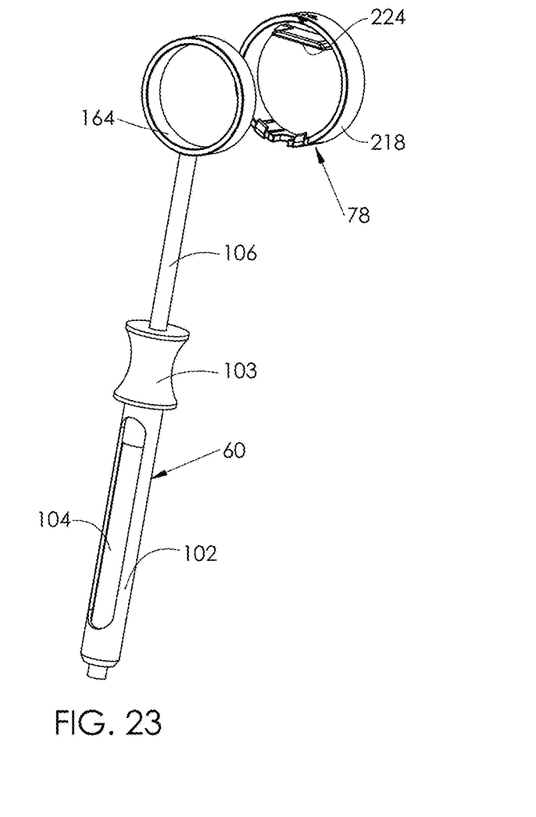
FIG. 23 is an isometric view of snap ring assembled with the syringe ring of an eighth embodiment.
Figure 24:
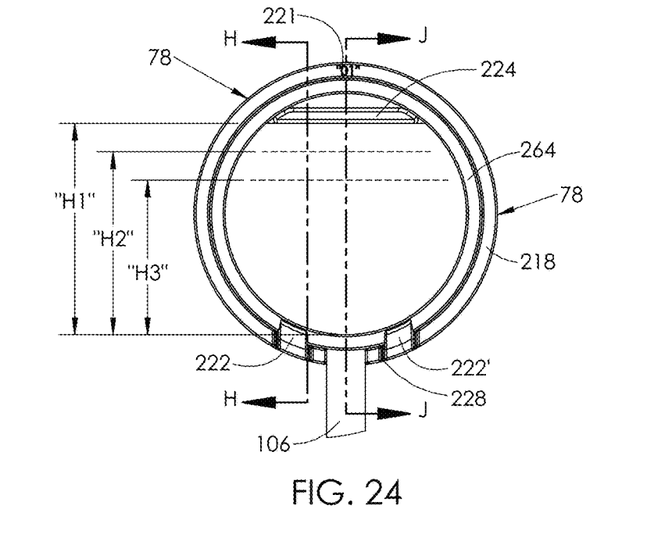
FIG. 24 is a front elevation view of a snap ring of the eighth embodiment.
Figure 25:
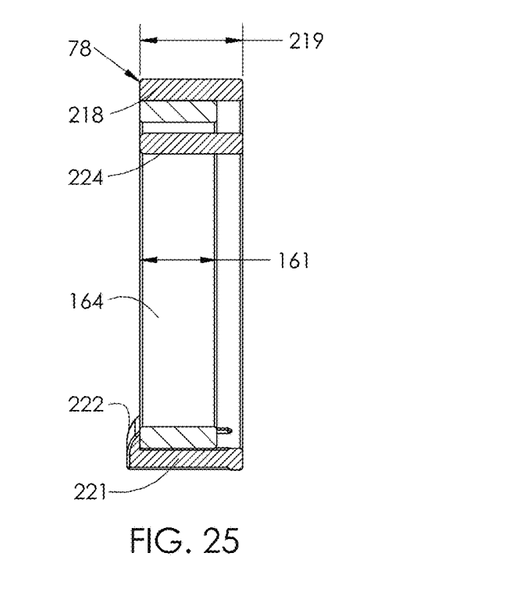
FIG. 25 is a sectional view H-H taken from FIG. 24 of the eighth embodiment.
Figure 26:
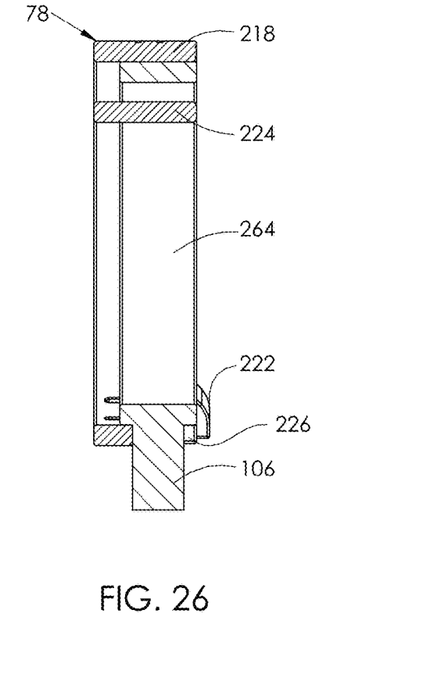
FIG. 26 is a sectional view J-J taken from FIG. 24 of the eighth embodiment.
Figure 27:
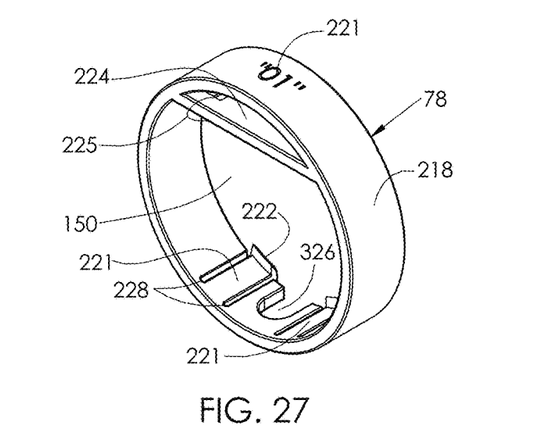
FIG. 27 is an isometric view of a snap ring of one side of the eighth embodiment.
Figure 28:
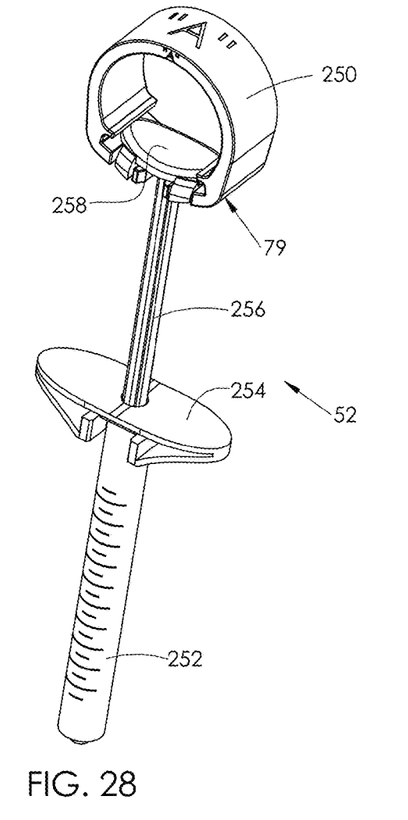
FIG. 28 is an isometric view of a snap body assembled with the syringe of a ninth embodiment.
Figure 29:
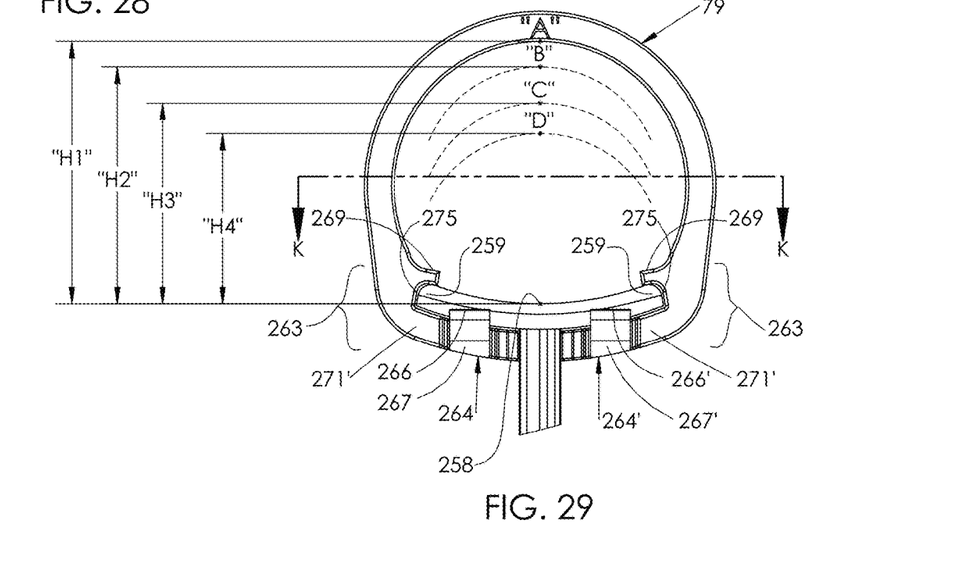
FIG. 29 is a front elevation view of a snap body assembled with plunger flange of the ninth embodiment.
Figure 30:
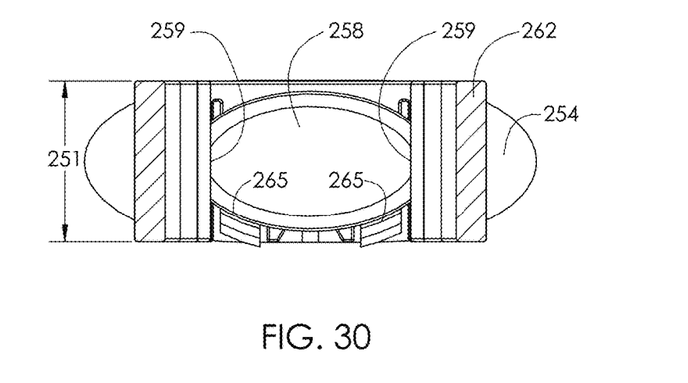
FIG. 30 is a sectional view K-K taken from FIG. 29 of snap body of the ninth embodiment.
Figure 31:
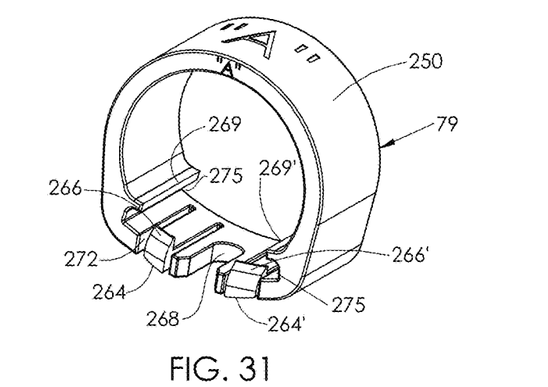
FIG. 31 is an isometric view of the snap body of the ninth embodiment.
Figure 32:
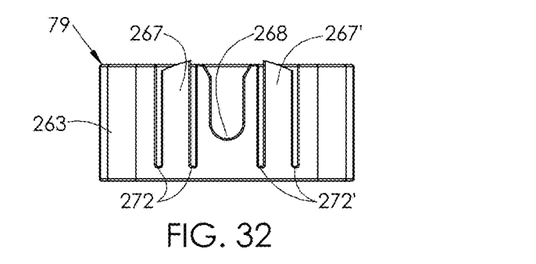
FIG. 32 is a bottom view of a snap body of the ninth embodiment.

A seventh embodiment 77 is shown in FIGS. 20-22 that comprises the annular member 164 connected to a syringe plunger shaft 106 via a shoulder 133 and has a lateral width 191, around which facing spacers 192, 194 are applied to together grip the annular member 164 when a screw 198 engages a threaded opening 197 (or other device) draws the spacers 192, 194 together and apply a compression force to the annular member 164. Typically, the facing spacers 192, 194 form a recess e.g. 199, by radially extending members 193, 195 that extend radially past, and as shown in cross section G of FIG. 22, partially surround the annular member 164. According to embodiments of the present invention, spacers 192, 194 may have a larger inwardly facing dimension to intrude further into the open area 150 to provide different interior spacings, e.g. H1, H2, H3, etc. as desired.

A single-piece, clip-on eighth embodiment 78 is shown in FIGS. 23-27, comprising a snap ring 218 that substantially surrounds the annular member 164 connected to syringe 60 plunger shaft 106 and has an inside spacing member 224 disposed within that is connected to the snap ring 218 and connected by relatively narrow connections 225. The single-piece substantially annular snap ring 218 has a lateral width 219 an inner dimension selected to receive annular member 164 therein and extend beyond annular member 164 lateral width 161. The lateral width of the connections 225 is typically the difference between the lateral width 219 and lateral width 161, and the connections 225 permits the inside spacing member 224 to be disposed within, and provide a selective reduction of the annular ring inner area 150 to lesser dimensions H1, H2, H3, FIG. 24, by choosing correspondingly different snap rings 218 sizes, as may be identified 221.

The snap ring 218 includes a recess 236 into the lateral dimension and substantially opposite to the spacing member 224, to accommodate the plunger shaft 106. The snap ring 218 is retained on the annular member 164 by resilient clips 221 disposed adjacent the recess 236 and formed from the snap ring 218 by slots 228 in the snap ring 218, better shown in FIG. 27, and further include inwardly oriented teeth 222 and 222' having slanted leading surfaces to urge radially outward displacement as the snap ring is applied to the annular member, and abrupt, substantially perpendicular inner surfaced to engage and retain the edge of the annular member against forces to laterally dislodge the snap ring 218.

A ninth embodiment 79 also comprising a snap ring, but in this embodiment, the novel snap ring 250 is shaped to engage as syringe 52 plunger 256 flange 258, as shown in FIGS. 28-33. The syringe 62 may typically comprise a disposable syringe with syringe barrel 252 having outward extending barrel flanges 254, and a plunger 256 having a finger flange 258 wherein the associated finger ring 250 surrounds the operator finger and is joined to and locks with the syringe plunger 256 flange 258 by a snap body portion 263 of the finger ring 250 that can be snapped onto the syringe plunger 256 and captures the syringe plunger flange 258. Snap body portion 263 includes a plunger flange holders 269 and 269'protrusions extending from the inner surface of the finger ring 250 disposed apart from an inner surface of an adjacent curved wall portion 271 to form recesses 275 and 275' to laterally (in the direction of ring 250 width 251) receive an outer portion 259 of the plunger flange 258 periphery to engage and prevent the displacement of snap 250 body in axial (defined by plunger 256 direction of movement) direction. Snaps 264, 264' are abruptly raised inner surfaces of protrusions 265 at the end of elongated spring-like members 267, 267' formed in the snap 250 body by slots 272, 272' in the snap 250 body, and may be angled or curved to mate or tangentially touch the shape of the facing plunger flange 258 surface shape (e.g. oval). The snaps typically have a sloped outer surface 266, 266' to urge displacement of the snaps 264, 264' as the snap is inserted over the plunger flange 258. The protrusions 265, 265' of the snaps project toward the plunger flange 258 body from the edge and prevent flange 258 lateral displacement from the syringe ring of embodiment 79 in the direction of the recess 268 opening which receives the plunger 256 shaft and prevent displacement from the finger ring 250. Snap rings 250 of different circumferences are selected to accommodate different inside dimensions (e.g. H1, H2, H3, H4) of finger ring 250 allow comfortable, close fitting, and secure syringe aspiration and compression strokes for different fingers size in a correspondingly selected size finger ring 250 opening 280.

Figure 33:
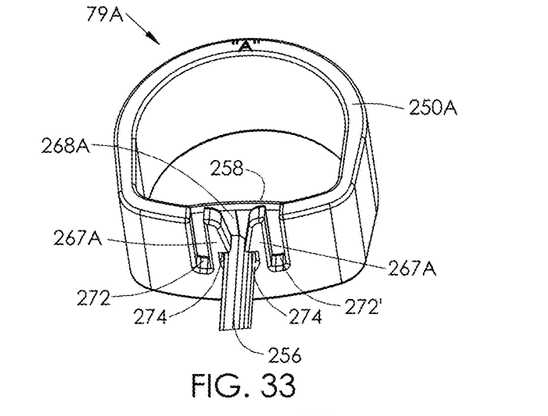
FIG. 33 is a perspective view of the snap body and plunger of a variant of the ninth embodiment.
Figure 34:
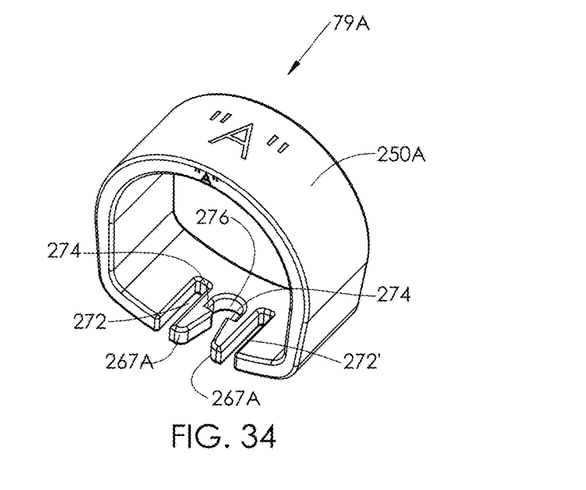
FIG. 34 is a bottom perspective view of a snap body of the variant of the ninth embodiment of FIG. 33.

A variation 79A of the ninth embodiment according to the present invention is shown on FIGS. 33-34, wherein the substantially annular snap ring 250A is secured to the plunger shaft 256 through a recess 268A defined by adjacent resilient members 267A, 267A' formed from a portion of the annular snap ring 250A by recesses 272, 272' partially into the snap ring 250A width. At least one of adjacent resilient members 272, 272A' includes an abrupt 'barb'-shaped protruding surface 274 extending toward the recess 268A such that the recess 268A opening outwardly has an initially larger dimension that gradually (as proceeding into the recess 268A) diminishes, then increases again in moving to a terminal dimension 276 as the recess inwardly ends, to receive the syringe shaft 256 that displaces the retention protrusion(s) 274 and be captured (and 'snap-in' when the protrusions have abrupt, barb-like reduction in width) at the terminal dimension. The flange 258 shaft-side surface faces and engages the inner side of the snap ring 250, which (in this and other embodiments) allows an upward finger force to be applied to lift the shaft-side surface of the flange 258 and allow the syringe to intake a substance, while permitting a reverse finger force to be directly applied to the flange 258 to discharge syringe substance. In one embodiment, the syringe shaft 256 below the flange 258 comprises a non-circular cross-section (e.g. slotted, flattened, oval, etc.) region and the terminal dimension region 276 of the recess has a complementary shape to mate with and resist relative rotation of the syringe shaft in the snap ring 250A. As with embodiment 79, snap rings 250A of different circumference (and may be labeled "A", "B", "C", "D", etc. accordingly) may be chosen to fit different size fingers and particular flange 258 facing shapes, and accordingly provide different internal opening heights (H1, H2, H3, etc. as shown for other embodiments).

Figure 35:
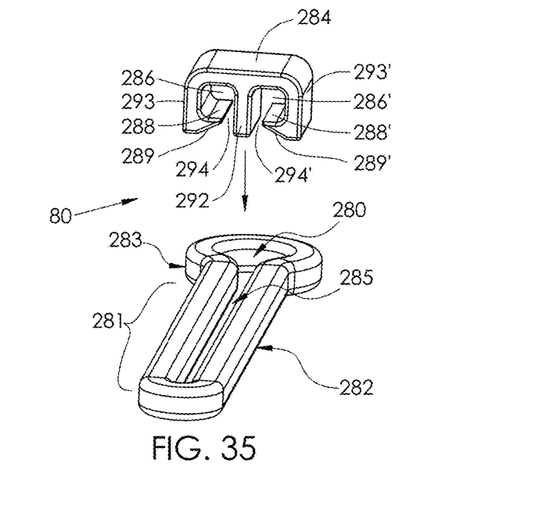
FIG. 35 is an exploded view of a tenth embodiment of the present invention.
Figure 36:
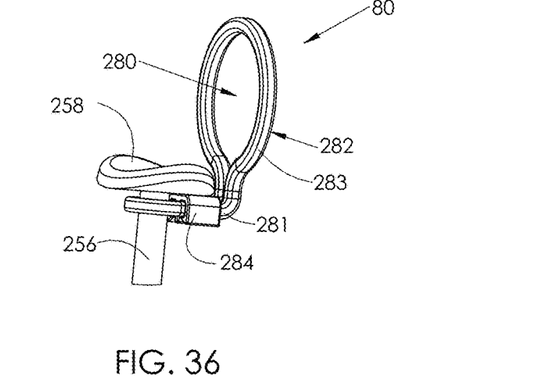
FIG. 36 is a perspective view of the tenth embodiment applied to a syringe plunger flange.

A tenth embodiment 80 of a finger ring is shown in the exploded view of FIG. 35 and the perspective view of FIG. 36, and comprises a deformable member 282 having a generally elongated portion 281 connected to an open loop region 283 having open area 280 into which a finger may be inserted. The elongated portion comprises at least two members separated to form an elongated space 285. In the embodiment of FIGS. 35, 36, the material of one or both portions 281 and 283 comprise a generally flaccid material to a deformable semi-rigid material adaptable to form the embodiment as described. As shown in FIG. 35, the elongated portion 281 is applied to and deformable to substantially surround a syringe plunger shaft 256 below the plunger flange 258. A clip 284 is applied to the elongate portion 281 to engage and retain the separated members of portion 281 (separated by space 285) and draw the separate members to conform around the shape syringe plunger shaft 256 to be captive and allow the open loop portion 283 to be moved out of the plane where the generally elongated portion is disposed, and provide an upward engaging force against the syringe-side of the flange 258 to be applied via the loop region 283 of the embodiment 80.

As provided in FIG. 35, the clip 284 exemplary embodiment is generally "E" shaped with a central extension 292 is separated from generally parallel extending members 293, 293' forming spaces 294, 294' therebetween, into which the separate (by space 285) members of region 281 are received when the clip is applied to the deformable member 282. As with other embodiments (e.g. 264, 264'), the parallel extending members 293, 293' include abruptly extending inward, tooth-like surfaces 288, 288' (typically at least 90 from the inner surface of members 293, 293') to retain the portion 281 therein, and sloped outer surfaces 289, 289' to allow the separated members into the spaces 294, 294' by deforming the separated members and/or urging the parallel extending members to separate to allow the separated members into the open areas 286, 286' beyond the inward surfaces 288, 288' and therein substantially captive to allow clip 284 to grip opposing surfaces of, and be retained on parallel members of the elongated portion. While the particular embodiments of FIGS. 35 and 36 show an initial configuration (i.e. resembling a 'keyhole'), and an "E"-shaped clip 284 is shown, other embodiment are also envisioned as may be made and used according to this novel finger ring.

The ring body(s) of the above embodiments as well as the components of other rigid or semi-rigid embodiments described herein can be fabricated by injection molding from different plastics such as Polypropylene, ABS, Polycarbonate or other materials that can be formed and function as described herein. Flexible embodiments may be made of cord or tape made from non-stretchable fabric, semi-rigid structures, or bendable metal, etc., or functionally equivalent. Further embodiments, modifications and substitutions by one of ordinary skill in the art are within the scope of the present invention which is not limited except according to the claims as follows.

What is claimed is:

1. A syringe, comprising:
   a syringe body capable of having a volume of material therein;
   a plunger disposed to enter the syringe body and dispense said material from said syringe body by movement of said plunger;
   a finger ring having an open area within said finger ring, being connected to said plunger and adapted to receive a finger within said open area; and
   a spacer inserted within said open area to selectively reduce said open area, wherein
   said spacer is disposed at a position relative to said finger ring and within said open area, is retained by a screw which engages said finger ring, and is adjustable to selectably adjust said open area wherein said screw is movable radially with respect to said finger ring.

2. The syringe of claim 1, wherein said finger ring comprises an outer surface, and is radially outwardly connected to said plunger at a point on said finger ringer outer surface, and said spacer is disposed within said open area radially opposite to said point at which said plunger is connected.

3. The syringe of claim 2, wherein said finger ring comprises a width, and said spacer further comprises a plurality of radially outward extending members extending from said open area and disposed to engaged said width across said outer surface.

4. The syringe of claim 1, wherein said plunger includes a threaded end and said finger ring includes a threaded region to receive said threaded end.

5. The syringe of claim 1, wherein said finger ring includes a threaded aperture to receive said screw.

6. The syringe of claim 5, wherein said screw comprises a proximal end inserted into said open area and a distal end having an enlarged region, said spacer comprises a compression member attached to said proximal end having an area wider than said proximal end.

7. The syringe of claim 6, wherein said compression member is radially captive onto said proximal end.

8. The syringe of claim 6, wherein said compression member is insertable into said open area.

* * * * *